(12) United States Patent
Yao et al.

(10) Patent No.: US 7,532,747 B2
(45) Date of Patent: May 12, 2009

(54) METHOD AND APPARATUS FOR ULTRASONIC IMAGING IN MMODE

(75) Inventors: Bin Yao, Nanshan (CN); Jian Dong, Nanshan (CN); Yong Li, Nanshan (CN)

(73) Assignee: Shenzhen Mindray Bio-Medical Electronics Co., Ltd., Nanshan, Shenzhen (CN)

( * ) Notice: Subject to any disclaimer, the term of this patent is extended or adjusted under 35 U.S.C. 154(b) by 715 days.

(21) Appl. No.: 11/323,701

(22) Filed: Dec. 30, 2005

(65) Prior Publication Data

US 2007/0049828 A1 Mar. 1, 2007

(30) Foreign Application Priority Data

Aug. 29, 2005 (CN) .................... 2005 1 0036992

(51) Int. Cl.
*G06K 9/00* (2006.01)
(52) U.S. Cl. .................. 382/128; 128/922; 378/4; 367/87; 600/441
(58) Field of Classification Search ............... 382/100, 382/128, 129, 130, 131, 132; 128/922; 378/4–27; 367/87, 89, 90, 93, 94; 342/171; 600/440, 600/441, 453, 455
See application file for complete search history.

(56) References Cited

U.S. PATENT DOCUMENTS

| | | | | |
|---|---|---|---|---|
| 4,398,540 A | * | 8/1983 | Takemura et al. | ........... 600/441 |
| 5,090,411 A | * | 2/1992 | Higuchi | ...................... 600/441 |
| 5,235,534 A | * | 8/1993 | Potter | ......................... 708/300 |
| 5,513,640 A | * | 5/1996 | Yamazaki et al. | ........... 600/455 |
| 5,544,654 A | * | 8/1996 | Murphy et al. | ............... 600/443 |
| 5,568,812 A | * | 10/1996 | Murashita et al. | ........... 600/440 |
| 5,820,561 A | * | 10/1998 | Olstad et al. | ................. 600/453 |
| 6,589,175 B2 | * | 7/2003 | Prater et al. | .................. 600/443 |

FOREIGN PATENT DOCUMENTS

| | | |
|---|---|---|
| CN | 1589747 A | 3/2005 |
| CN | 1599578 A1 | 3/2005 |
| CN | 1662181 A | 8/2005 |
| JP | 09-147134 | 6/1997 |

\* cited by examiner

*Primary Examiner*—Anand Bhatnagar
(74) *Attorney, Agent, or Firm*—Kory D. Christensen; Stoel Rives LLP

(57) ABSTRACT

The present invention provides a mmode imaging method and apparatus for an ultrasonic diagnosis device to increase the continuity of the displayed mmode images. The mmode imaging method of the invention comprises steps: define a sample line on a frame of bmode image, so as to select bmode data of sample points constituting the sample line; convert the bmode data of the sample points obtained from two consecutive frames of bmode image into two of mmode lines arranged in time order in a mmode image; at predetermined positions between the two mmode lines, generate mmode data that constitute at least one mmode lines based on the echo data of corresponding sample points on the two mmode lines; and image the mmode data in time sequence.

18 Claims, 5 Drawing Sheets

METHOD AND APPARATUS FOR ULTRASONIC IMAGING IN MMODE

TECHNICAL FIELD

The present invention relates to a method and apparatus for ultrasonic imaging in mmode used in an ultrasonic diagnosis system, more particularly, to an ultrasonic imaging method and apparatus for generating mmode displays from bmode data for generating bmode displays.

BACKGROUND OF THE INVENTION

Ultrasonic imaging is a method for imaging the interior structure of a living body, such as a human body, by transmitting ultrasonic into a human body and receiving echoes reflected from interfaces between tissues and organs having different acoustic characteristic impedances and imaging them based on the received echoes.

A bmode ultrasonic diagnosis device scans a living body one dimensionally with ultrasonic beams transmitted from a probe so as to image a cross section of tissues or organs being scanned. On the displayed cross section, brightness of points indicates amplitudes of echo signals (lighted points), X-axis demonstrates a distance over which the ultrasonic beams scan, and Y-axis demonstrates a detected depth into the tissues or organs.

A conventional mmode ultrasonic diagnosis device which provides images of time-motion type is generally used for observing the motion of a heart. In an operating status, a probe transmits ultrasonic beam from a fixed position and in a certain direction and receives the echo signals. On a mmode display, the brightness of each point constituting the display is proportional to the amplitude of the echo from the depth represented by the point. The Y-axis coordinate of each point represents the depth into a heart, for example, and the X-axis coordinate indicates time at which the data for that point is measured. Therefore, a mmode display shows traces of movement of tissues of a heart.

Modern ultrasonic diagnosis devices often show bmode and mmode together on the same display. By defining positions that need to be detected by a mmode probe on a bmode cross-section display, and detecting along the defined positions with a mmode probe, desired mmode images are obtained.

However, during a conventional mmode imaging process, due to the presence of lung or ribs, it's difficult to orient the ultrasonic beam transmitted from a probe to be normal to the wall of the heart being detected, which will deteriorate the accuracy of the resultant data; further, the heart cannot keep being in a constant angle from the ultrasonic beam, as a result, the echo signal from a same position on the surface of the heart has a varying intensity, that is, the displayed trace of movement of the surface of the heart has varying brightness, which in the worst cases might negatively affect judgment of a medicine doctor.

A patent application U.S. Pat. No. 6,589,175 B2 by PHILIPS discloses a mmode ultrasonic imaging method and apparatus, in which ultrasonic beams are transmitted and echoes are received to form conventional mmode images in the time intervals of producing a plurality of frames of bmode images, inevitably it will occupy the time originally for producing bmode images. To some extent, the method and apparatus overcome the above-mentioned defaults of conventional mmode images, however it lowers the frame rate of bmode images, and obviously degrades the performance of apparatuses having low frame rate of bmode images.

Recently there is introduced an anatomical mmode or arbitrary mmode ultrasonic imaging method and apparatus. In this method, based on a sample line defined by a user on a displayed bmode image, bmode data (i.e., detected depth of echo signals and brightness corresponding to the amplitudes of the echoes) corresponding to each sample point included in the sample line are selected from each frame of bmode image. Then convert the bmode data selected from each frame of bmode image into a mmode line corresponding to a certain time in a mmode image, so as to produce a plurality of mmode lines arranged in time order to show the traces of movement of the interfaces that the sample line goes across.

However, in the case that the bmode images are measured at low frame rate, when producing anatomical mmode images from the bmode data, there will be a relatively big interval between adjacent mmode lines in a mmode image, as a result, the traces displayed in a mmode image are not continuous visually. This is not satisfying for observing organs such as a heart that moves fast.

DISCLOSURE OF THE INVENTION

One aspect of the invention is to provide a method and apparatus for ultrasonic imaging in mmode, by which the continuity of mmode images which are obtained based on low frame rate bmode data is increased.

A mmode imaging method according one embodiment of the invention comprises steps:

(a) defining a sample line on a frame of bmode image, so as to select bmode data of sample points constituting the sample line;

(b) converting the bmode data of the sample points obtained from two consecutive frames of bmode image into two of mmode lines arranged in time order in a mmode image;

(c) at predetermined positions between the two mmode lines, generating mmode data that constitute at least one mmode lines based on the echo data of corresponding sample points on the two mmode lines;

(d) imaging the mmode data in time sequence.

The other aspects and effects of this invention will be apparent and the present invention will be fully understood through the description taking reference to the following drawings.

BRIEF DESCRIPTION OF THE DRAWINGS

The embodiments of the invention will be described in detail with reference to the drawings, wherein.

Figure 1A:
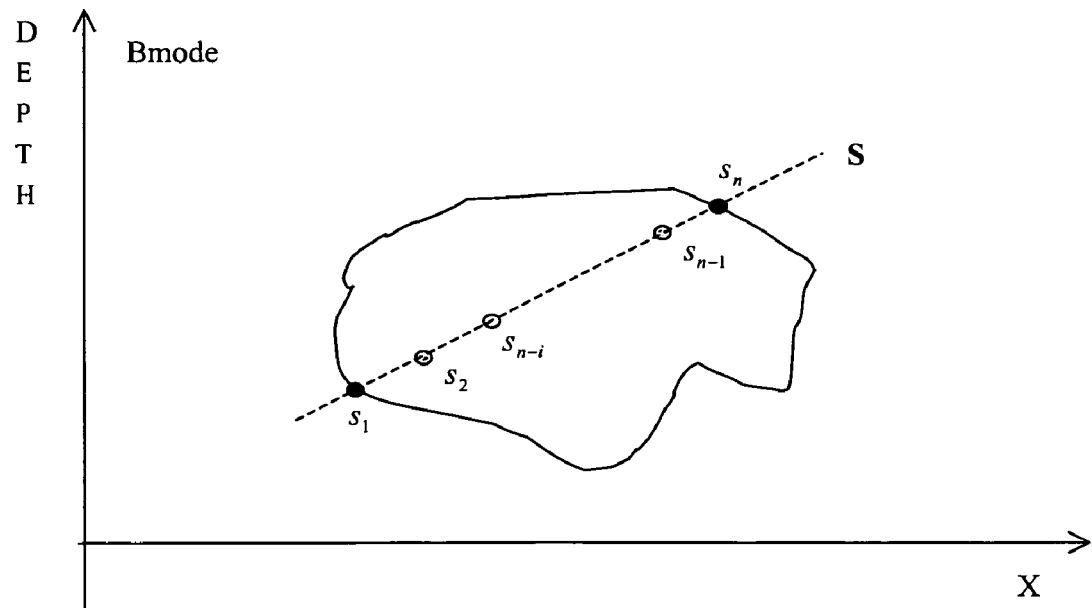
FIG. 1A is a simplified diagram showing a defined sample line on a displayed bmode image according to one embodiment of the invention.

In all the drawings, the same reference signs identify the same or corresponding features or functions.

EMBODIMENTS

According to the mmode imaging method of this invention, first, define a sample line on a bmode image, and convert bmode data corresponding to the sample points constituting the sample line in each frame of bmode image into mmode lines in sequence of time. Then, produce mmode data of one or more mmode lines based on the echo data (i.e., detected depth of echo signals and brightness corresponding to the amplitudes of the echoes) of corresponding sample points on two adjacent mmode lines. Finally, interpolate the produced mmode lines between the two adjacent mmode lines so that the continuity of displayed mmode images is increased visually.

Next the mmode imaging method of this invention will be described in detail referring to the drawings.

As shown in FIG. 1A, a sample line S is defined on a bmode image, including sample points s1, $s_2$, ... $S_{n-j}$ ... $S_{n-1}$, $S_n$.

Figure 1B:
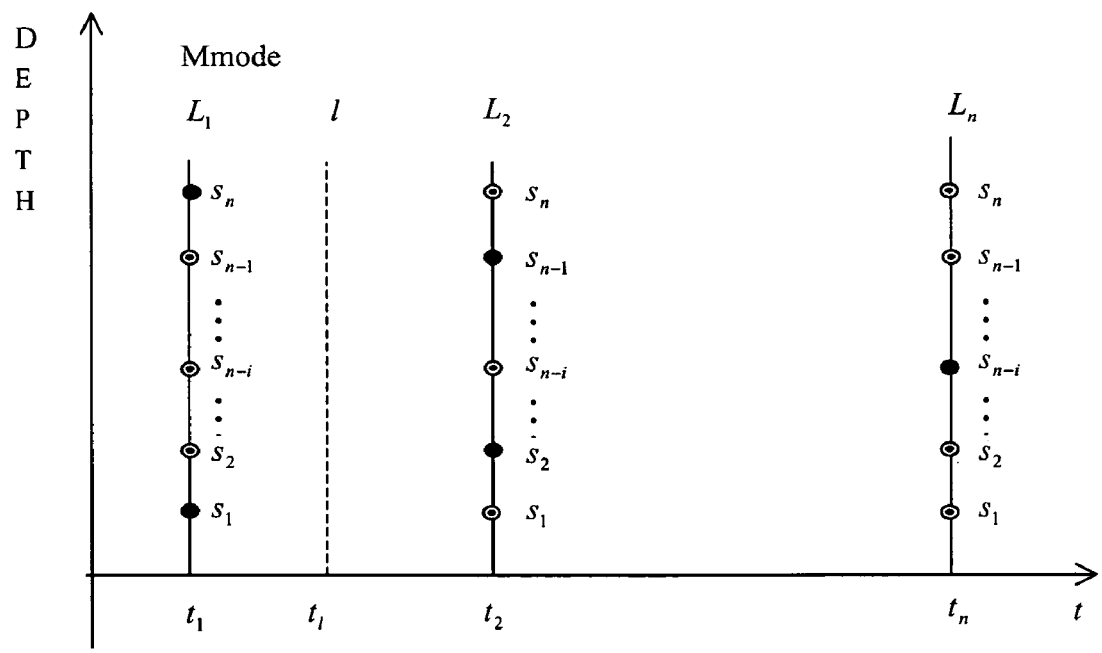
FIG. 1B is a schematic diagram showing a mmode image converted based on bmode images according to one embodiment of the invention.

Convert bmode data at sample points $s_1, s_2, \ldots S_{n-j} \ldots S_{n-1}$, $S_n$ of each frame of bmode image at time $t_1, t_2, \ldots t_n$ into mmode lines $L_1, L_2, \ldots L_n$ at respective time, so that a mmode image is obtained as shown in FIG. 1 B, which shows the changes of the sample line S over time.

According to the present invention, based on the above converted mmode lines $L_1, L_2, \ldots L_n$, with use of echo data of corresponding sample points included in two adjacent mmode lines respectively, several mmode lines (such as mmode line l shown by dashed line in FIG. 1 B) are produced and interpolated between the two adjacent mmode lines, therefore, without lowering the frame rate of bmode images, the sample line S is shown with a desired continuity over time even in the case of low frame rate of bmode images.

Figure 2:
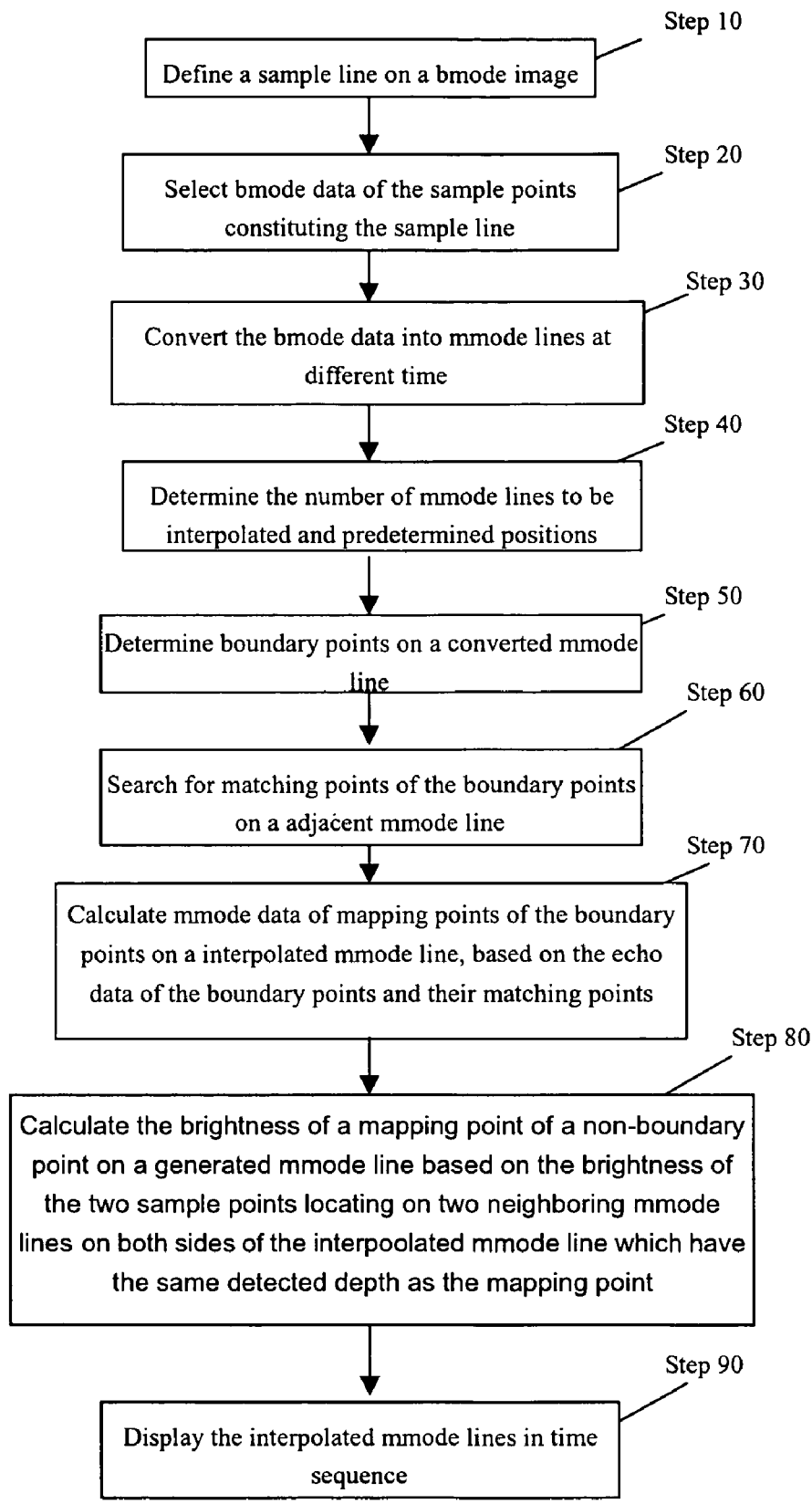
FIG. 2 is a flowchart showing steps for producing continuous mmode images based on bmode data according to one embodiment of the invention.

Now the method of producing continuous mmode images based on bmode data will be described with reference to FIG. 2.

1. Convert a sample line in a bmode image into mmode lines

First, define a sample line in a bmode image (step 10). Select bmode data at each sample points composing the sample line from each frame of bmode image (step 20). Convert the bmode data selected from each frame of bmode image into mmode lines corresponding to different times in a mmode image (step 30).

2. Interpolate mmode lines between two adjacent mmode lines

Based on an expected frame rate of mmode lines, determine the number of mmode lines to be interpolated between two adjacent mmode lines, and subsequently determine the coordinates on the time axis of each mmode line to be interpolated based on the number of mmode lines (step 40).

Next, take an arbitrary mmode line as an example to determine boundary points in the mmode line whose brightness notably increases and which represent boundaries of tissues or organs within a human body (step S50).

In an embodiment of the invention, a boundary point is found by evaluating brightness of a group of neighboring sample points, specifically by taking the following steps, select a plurality of sample points neighboring a certain sample point on the mmode line as a sample point group, then, further select a part of the sample point group neighboring said certain sample point as a sample point subgroup. Evaluating the brightness of each sample point included in the sample point group and the subgroup to judge whether said certain sample point is a boundary point. Details of the judgment will be described in an embodiment with reference to FIG. 3.

Then, as for a boundary point, based on the brightness of the point and its neighboring points, by a similarity searching method, search for a matching point in an adjacent mmode line which best matches with the boundary point (step 60). The process of searching for a matching point will be described in a following embodiment with reference to FIG. 3.

The boundary point and its matching point define a movement vector starting at the boundary point ending at the matching point. The intersection point of the movement vector with the interpolated mmode line can be viewed as a mapping point of the boundary point on the interpolated mmode line The mmode data at the mapping point is calculated based on those of the boundary point and its matching point, so as to obtain Y-axis coordinate and brightness of the mapping point (step 70).

Besides mapping points of boundary points, the interpolated mmode line also includes mapping points of non-boundary points.

As for a mapping point of non-boundary point, its brightness could be calculated based on the brightness of two sample points included in two immediate neighboring mmode lines respectively, which locate at the same depth as the mapping point of non-boundary point (step 80).

Details in calculating the brightness of mapping points of boundary points and non-boundary points will be described in a following embodiment with reference to FIG. 3.

3. Display the generated mmode images

After mmode data are generated following the above described steps, via a conventional mmode image display device, the interpolated mmode lines can be displayed in sequence of time, as a result, the displayed mmode images have better continuity (step 90).

Next the method for generating continuous mmode images based on bmode data will be described with reference to FIG. 3.

Figure 3:
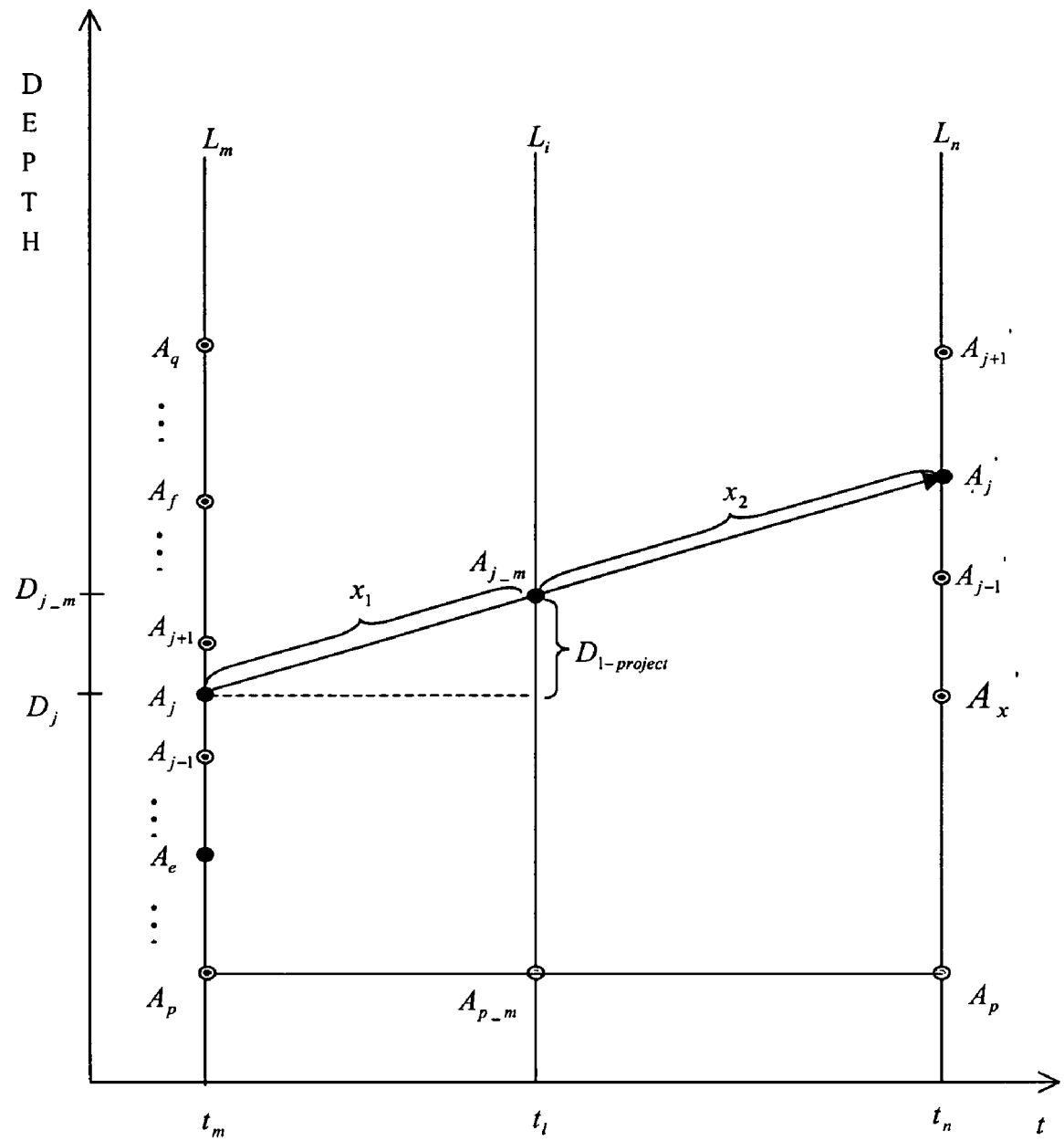
FIG. 3 is a schematic diagram demonstrating the principle for producing continuous mmode images based on bmode data according to one embodiment of the invention.

In FIG. 3, $L_m$ and $L_n$ represent the same sample line defined on a bmode image, but converted from two consecutive frames of bmode image.

Here, the process of generating mmode data will be introduced by taking an example that one mmode line $L_i$ is interpolated between mmode lines $L_m$ and $L_n$.

First boundary points on mmode line $L_m$ are determined.

A sample point $A_j$ on $L_m$ is selected. Define a plurality of sample points $A_p, \ldots A_{j-1}, A_j, A_{j+1}, A_q$ at neighboring positions in the mmode line $L_m$ as a sample point group, and define a part of the group Ae, ... $A_{j-1}, A_j, A_{j+1}, A_f$ at neighboring position of the sample point $A_j$ as a subgroup, wherein, p, q, j, e, f are integers, and satisfying p<e, f<q.

If the number of background points in the sample point group which have brightness smaller than a threshold is larger than a predetermined value, and the number of non-background points in the subgroup which have brightness larger than a threshold is larger than another predetermined value, then define the sample point $A_j$ as a boundary point.

For example, the sample point group includes 10 sample points (q−p+1=10), and the subgroup includes 3 points (f−e+1=3), if more than 50% of sample points in the sample point group are background points, and more than 50% of sample points in the sample point subgroup are non-background points, then sample point $A_j$ is judged as a boundary point.

Next, through a similarity searching method, search for a matching point $A'_j$ of the boundary point $A_j$ on mmode line $L_n$.

Select g sample points on each side of point $A_j$ on the mmode line $L_m$, which are neighboring to point $A_j$, which, including point $A_j$, compose a sample point group of 2g+1 sample points in total, i.e., $A_{j-g}, \ldots A_j, \ldots, A_{j+g}$.

On the mmode line $L_n$, for a plurality of sample points, select g sample points on each side of an individual point in a similar manner so as to form a plurality of candidate sample point group, each including 2g+1 sample points.

Calculate the brightness difference between each point in the sample point group including point $A_j$ and its corresponding point in a candidate group respectively. For example, it is assumed that one candidate group includes $A_{h-g}', \ldots A', \ldots, A_{h+g}'$, with point $A_h'$ locating at the middle, then calculate the brightness difference between $A_{j-g}$ and $A_{h-g}', \ldots A_j$ and $A_h', \ldots, A_{j+g}$ and $A_{h+g}'$.

Calculate the sum of the absolute value of the brightness difference for each candidate group, find the one having a minimum sum value which is considered as having most similar brightness distribution to the sample point group having $A_j$ as its middle point, and the middle point of the candidate group is judged as the matching point of the point $A_j$. For instance, if the candidate group including point $A_h'$ has a minimum sum value, then $A_h'$ is the matching point on the mmode line $L_n$ of $A_j$.

To find the matching point more quickly, it is possible to choose those points positioned at the same depth as or in a certain range around depth of the selected boundary point as middle points for each candidate group. For example, on the mmode line $L_n$, choose sample point $A_x'$ at the same depth as point $A_j$ and 10 sample points in the neighboring region of $A_x'$ as the middle points of respective candidate group.

Further, to calculate the mmode data of a mapping point of a boundary point more accurately, it's possible to correct the mmode data of the matching point based on neighboring sample points of the boundary point and the matching points of the neighboring sample points on a mmode line $L_n$.

For example, a boundary point $A_j$ and its neighboring points $A_{j-1}$ and $A_{j+1}$ are determined to have matching points $A_j', A_{j-1}'$ and $A_{j+1}'$ respectively through the above mentioned process. Since the boundary point $A_j$ is positioned between sample points $A_{j-1}$ and $A_{j+1}$, subsequently, the matching point $A_j'$ shall be positioned between matching points $A_{j-1}'$ and $A_{j+1}'$.

If it's detected that the point $A_j'$ is not positioned between $A_{j-1}'$ and $A_{j+1}'$, it might be noise data or the like that cause $A_j'$ deviate from its true position. By setting the point $A_j'$ between $A_{j-1}'$ and $A_{j+1}'$, the errors of the position matching points are reduced.

After the matching point $A_j'$ of the boundary point $A_j$ is determined, points $A_j$ and $A_j'$ define a movement vector, as shown in FIG. 3. The movement vector intersects with the mmode line $L_n$ at $A_{j-m}$, which is considered as a mapping point of the boundary point $A_j$ on the mmode line $L_n$.

Afterwards, calculate the mmode data of the mapping point (such as $A_{j-m}$) based on the corresponding boundary point and the matching point (such as $A_j$ and $A_j'$). The mmode data includes detecting depth and brightness.

The following describes one of the methods for calculating the mmode data taking the mapping point $A_{j-m}$ as an example.

Assume a distance $x_1$ between the boundary point $A_j$ and the mapping point $A_{j-m}$, and a distance $x_2$ between the boundary point $A_j$ and the matching point $A_j'$ (see FIG. 3), then, The detected depth $D_{j-m}$ of the mapping point $A_{j-m}$ (i.e., the Y-axis coordinate of $A_{j-m}$) can be obtained by adding the detected depth $D_j$ of the boundary point $A_j$ (i.e., the Y-axis coordinate of $A_j$) with the projection of distance $x_1$ on the Y-axis $D_{j\_project}$, that is expressed as, $$D_{j-m} = D_j + D_{j\_project} \tag{1}$$

Round up the detected depth $D_{j-m}$ of the mapping point $A_{j-m}$ so as to obtain the Y-axis coordinate of a pixel corresponding to the mapping point $A_{j-m}$.

The brightness $B_{j-m}$ of the mapping point $A_{j-m}$, which is an average of the brightness $B_j$ and $B_j'$ of points $A_j$ and $A_j'$ weighted according to the distances x1 and x2 between $A_{j-m}$, $A_j$ and $A_j'$, and can be given by, $$B_{j-m} = \frac{x_2}{x_1 + x_2} B_j + \frac{x_1}{x_1 + x_2} B_j' \tag{2}$$

After obtaining the mmode data of the mapping points of respective boundary points, the mmode data of the mapping points on the interpolated mmode line of non-boundary points are calculated.

If the speed of the CPU is fast enough, similar process could be adopted for the non-boundary points as for the boundary points, that is, searching for a matching point on the mmode line $L_n$, and then calculating the mmode data of a mapping point based on the echo data of the non-boundary point and its matching point.

However, non-boundary points do not have notable changes in brightness, not represent boundaries of tissues and organs within a human body, compared to boundary points, non-boundary points do not provide as meaningful information. Thus, a simplified method could be used as following to determine the mmode data of a mapping point of a non-boundary point on an interpolated mmode line.

Referring to FIG. 3, it is assumed that $A_{p-m}$ is a mapping point of a non-boundary point on a interpolated mmode line $L_i$, then the brightness of point $A_{p-m}$ could be calculated based on the brightness of $A_p$ and $A_p'$, which have the same detected depth as the point $A_{p-m}$ and locate on mmode lines $L_m$ and $L_n$ on both sides of the interpolated mmode line $L_i$.

A similar method as that for calculating the brightness of a mapping point of a boundary point could be used for $A_{p-m}$, that is, to calculate an average of the brightness of points $A_p$ and $A_p'$ weighted according to the distances between $A_{p-m}, A_p$ and $A_p'$ as the brightness of point $A_{p-m}$; or simply take an algebraic average of the brightness of points $A_p$ and $A_p'$.

In the case of interpolating more than one mmode lines between two adjacent mmode lines, to obtain more accurate brightness for mapping points of non-boundary points on the interpolated mmode lines, it's possible to calculate the brightness of a mapping point of a non-boundary point based on the two points which have the same detected depth as the said mapping point and locate on a nearest mmode line and on a interpolated mmode line respectively.

Figure 4:
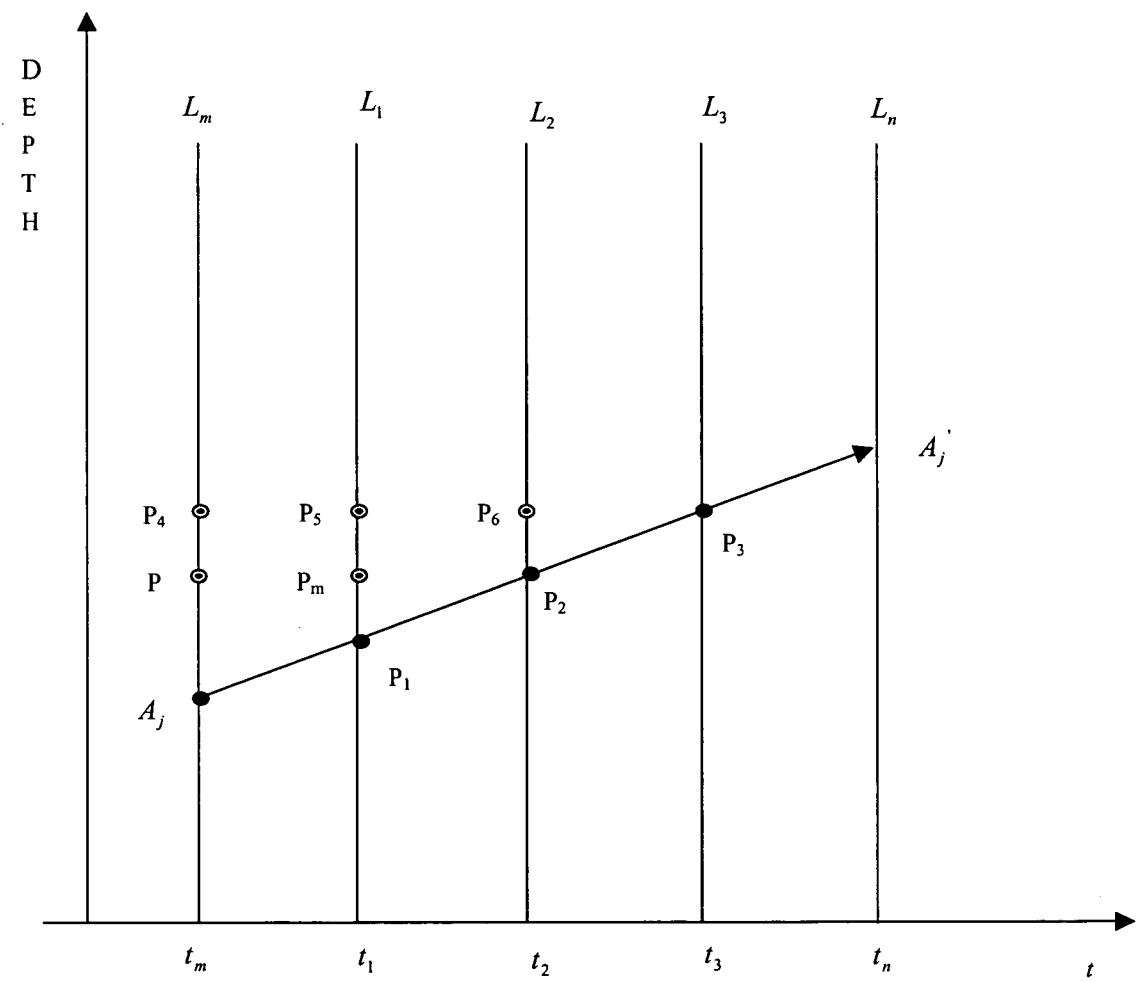
FIG. 4 is a schematic diagram demonstrating the principle for producing continuous mmode images based on bmode data according to another embodiment of the invention.

For example, 3 mmode lines $L_1, L_2$ and $L_3$ are interpolated between two mmode lines $L_m$ and $L_n$. As shown in FIG. 4, by way of a movement vector, 3 mapping points $P_1, P_2$ and $P_3$ of a boundary point $A_j$ on mmode lines $L_1, L_2$ and $L_3$ are obtained respectively. As for a mapping point $P_m$ of a non-boundary point on the mmode line $L_1$, its brightness could be calculated based on $P_2$ and another point P on the mmode line $L_m$, both of which have the same depth as $P_m$, and the brightness of the mapping points $P_2$ could be calculated by the above mentioned method by way of movement vector.

Similarly, the brightness of the mapping point $P_5$ of a non-boundary point could be calculated based on points $P_3$ and $P_4$ which locate at the same depth as $P_5$; the brightness of the mapping point $P_6$ of a non-boundary point could be calculated based on points $P_5$ and $P_3$ on the interpolated mmode lines $L_1$ and $L_3$ which locate at the same depth as $P_6$.

In conclusion, as for a mapping point of a non-boundary point on a interpolated mmode line, its brightness is preferably calculated based on two points on two mmode lines respectively which locate on both side of the mapping point, and the two points have the same depth as the mapping point.

Finally, after obtaining the brightness of all points constituting the interpolated mmode lines (such as $L_1$ in FIG. 3 and $L_1, L_2$ and $L_3$ in FIG. 4), display the interpolated mmode lines between mmode lines $L_m$ and $L_m$, so that the displayed mmode images looks more continuous.

Figure 5:
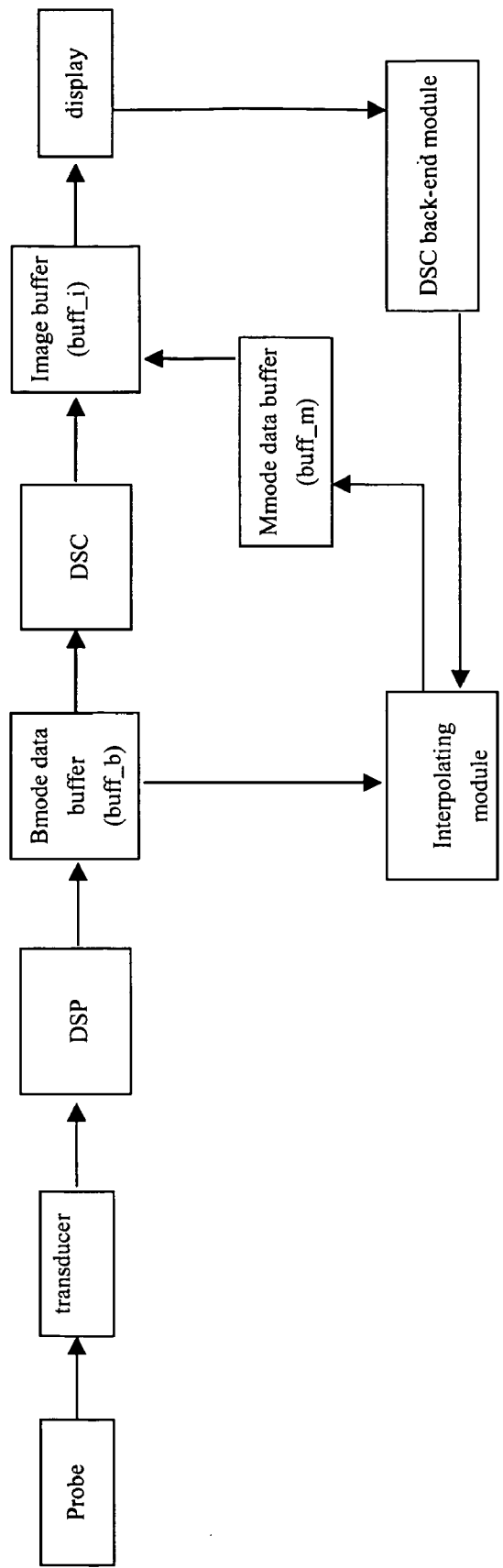
FIG. 5 is a block diagram showing the configuration of the apparatus for producing mmode images based on bmode images according to one embodiment of the invention.

FIG. 5 is a block diagram showing the configuration of an apparatus which produces continuous mmode images based on bmode data according to one embodiment of the invention. On the basis of a conventional bmode imaging apparatus, the following elements are added: a DSC (Digital Scan Conversion) back-end module, for converting the coordinates of each sample point included in a sample line defined on a bmode image displayed on a monitor into polar coordinate, so as to be consistent with the type of coordinates of bmode data stored in a bmode data buffer; an interpolation module, for reading out bmode data corresponding to each sample point from the stored each frame of bmode image, and converting them into respective mmode lines at different time in a mmode image, and interpolating one or more mmode lines between every two adjacent mmode lines; a mmode data buffer, for storing the interpolated mmode data of mmode lines, and supplying the stored mmode data to a display device via a image buffer (buff_i), so as to display the interpolated mmode lines in real time when displaying mmode images.

The functions of the DSC back-end module and the interpolation module can also be implemented by means of either software or hardware, or a combination thereof.

INDUSTRIAL APPLICABILITY

In accordance with the mmode imaging method and apparatus of the invention, bmode data from each frame of bmode image which corresponding to the sample points constituting a sample line defined arbitrarily on a displayed bmode image are converted into mmode lines in a sequence of time. One or more mmode lines are generated based on the echo signals of corresponding points on two adjacent mmode lines, and are interpolated between the two adjacent mmode lines, therefore, continuous mmode images with desired frame rate of mmode images could be achieved without lowering the frame rate of bmode images.

In practice, the technical solutions of the invention could be flexibly implemented and appropriately modified as needed. Those skilled in the art could understand that there should be various modifications to the mmode imaging method and apparatus disclosed by the invention without departing from the spirit of the invention. The scope of protection of the present invention shall be defined by the claims attached.

What is claimed is:

1. A mmode imaging method used for an ultrasonic diagnosis device, comprising steps:

using a processor to perform the steps of:

(a) defining a sample line on a frame of bmode image, so as to select bmode data of sample points constituting the sample line;

(b) converting the bmode data of the sample points obtained from two consecutive frames of bmode image into two of mmode lines arranged in time order in a mmode image;

(c) at predetermined positions between the two mmode lines, generating mmode data that constitute at least one mmode lines based on the echo data of corresponding sample points on the two mmode lines;

(d) imaging the mmode data in time sequence.

2. A mmode imaging method of claim 1, wherein, the echo data comprise brightness of the sample point and detected depth to which the sample point corresponds.

3. A mmode imaging method of claim 2, wherein step (c) includes:

(c1) based on the brightness of respective sample points on one of the two mmode lines, finding their matching points on another mmode line;

(c2) calculating mmode data of mapping points of the sample points on the generated mmode lines, based on the echo data of the sample points and their matching points, wherein the mapping point of a sample point on the generated mmode line is a point at which the generated mmode line intersects with the line section connecting the sample point and its matching point.

4. A mmode imaging method of claim 3, wherein step (c1) includes:

(c11) selecting a plurality of sample points at neighboring positions of a certain sample point on the mmode data line, so as to constitute a sample point group;

(c12) among said a plurality of sample points, selecting some of the sample points at neighboring positions of the certain sample point so as to constitute a sample point subgroup;

(c13) evaluating the brightness of each sample point included in the sample point group and the sample point subgroup, to judge whether the certain sample point is a boundary point;

(c14) if the certain sample point is judged as a boundary point, then searching for the matching point of the boundary point on the other mmode line.

5. A mmode imaging method of claim 4, wherein step (c13) includes:

in the sample point group, determining the number of background sample points whose brightness are smaller than a predetermined value;

in the sample point subgroup, determining the number of non-background sample points whose brightness are larger than a predetermined value;

if the number of background sample points and the number of non-background sample points are both larger than a predetermined number, defining the certain sample point as a boundary point.

6. A mmode imaging method of claim 4, wherein step (c14) includes:

(i) symmetrically selecting equal number of sample points on both sides of the boundary point at the neighboring positions of the boundary point, with the boundary point as a center, so as to constitute a sample point group which contains the boundary point;

(ii) on the other mmode line, with a plurality of sample points as center respectively, symmetrically selecting equal number of sample points on both side of each of the center point at the neighboring positions thereof, so as to constitute a plurality of candidate sample point groups, each of the candidate sample point group containing the center point respectively;

(iii) calculating the brightness difference between each sample point in the sample point group that contains the boundary point and a corresponding point in the candidate sample point group;

(iv) calculating the sum of the absolute value of the brightness difference for each candidate sample point group, defining the center point in a candidate sample point group having a minimum sum value of the absolute value of the brightness difference as a matching point of the boundary point.

7. A mmode imaging method of claim 6, wherein step (ii) includes:

on the other mmode line, selecting sample points in a certain depth range around the detected depth of the boundary point as said center points.

8. A mmode imaging method of claim 4, wherein step (c2) includes:

calculating the detected depths of the mapping points of the boundary points based on those of the boundary points and their matching points;

calculating the brightness of the mapping points of the boundary points, based on the distances between the boundary points and the mapping points of the boundary points and the distances between the matching points of the boundary points and the mapping points, and based on the brightness of those points.

9. A mmode imaging method of claim 4, wherein, the brightness of a mapping point of a non-boundary point on a generated mmode line depends on the brightness of the two sample points locating on two neighboring mmode lines on both sides of the generated mmode line which have the same detected depth as the mapping point of the non-boundary point.

10. A mmode imaging method of claim 4, further including steps, correcting matching points of the boundary points according to the matching points of the points at the neighboring positions of the boundary points.

11. A mmode imaging method of claim 1, wherein, the number of the mmode lines to be generated depends on an expected frame rate of the mmode images.

12. An apparatus for mmode imaging used for ultrasonic diagnosis devices, including:

a sampling unit, for defining a sample line on a frame of bmode image, so as to select bmode data of each sample point constituting the sample line;

a converting unit, for converting the bmode data of the sample points obtained from two consecutive frames of bmode image into two of mmode lines arranged in time order in a mmode image;

a generating unit, for generating mmode data that constitute at least one mmode lines based on the echo data of corresponding sample points on the two mmode lines at predetermined positions between the two mmode lines an imaging unit, for imaging the mmode data in time sequence.

13. An apparatus for mmode imaging of claim 12, wherein, the echo data comprise at least brightness and detected depth of the sample points.

14. An apparatus for mmode imaging of claim 12, wherein, the generating unit includes, a determining unit, for determining, based on the brightness of the respective sample points on one of said two mmode lines, the matching points on the other mmode line of said sample points;

a calculating unit, for calculating mmode data of mapping points of the sample points on the generated mmode lines, based on the echo data of the sample points and their matching points, wherein the mapping point of a sample point on the generated mmode line is a point at which the generated mmode line intersects with the line section connecting the sample point and its matching point.

15. An apparatus for mmode imaging of claim 14, wherein the steps performed by the determining unit comprise, selecting a plurality of sample points at neighboring positions of a certain sample point on the mmode data line, so as to constitute a sample point group;

among said a plurality of sample points, selecting some of the sample points at neighboring positions of the certain sample point so as to constitute a sample point subgroup;

evaluating the brightness of each sample point included in the sample point group and the sample point subgroup, to judge whether the certain sample point is a boundary point;

if the certain sample point is judged as a boundary point, searching for the matching point of the boundary point on the other mmode line.

16. An apparatus for mmode imaging of claim 15, wherein the steps performed by the determining unit further comprise, symmetrically selecting equal number of sample points on both side of the boundary point at the neighboring positions of the boundary point, with the boundary point as a center, so as to constitute a sample point group which contains the boundary point;

on the other mmode line, with a plurality of sample points as center respectively, symmetrically selecting equal number of sample points on both side of each of the center point at the neighboring positions of each of the center point, so as to constitute a plurality of candidate sample point groups, each of the candidate sample point group containing the center point respectively;

calculating the brightness difference between each sample points in the sample point group that contains the boundary point and a corresponding point in the candidate sample point group;

calculating the sum of the absolute value of the brightness difference for each candidate sample point group, defining the center point in a candidate sample point group having a minimum sum value of the absolute value of the brightness difference as a matching point of the boundary point.

17. An apparatus for mmode imaging of claim 15, wherein, the calculating unit calculates the detected depths of the mapping points of the boundary points based on those of the boundary points and their matching points, and calculates the brightness of the mapping points of the boundary points, based on the brightness of the boundary points and their matching points, and on the distances between the boundary points and the mapping points of the boundary points and the distances between the matching points of the boundary points and the mapping points.

18. An apparatus for mmode imaging of claim 15, wherein, the calculating unit calculates the brightness of a mapping point of a non-boundary point on a generated mmode line based on the brightness of the two sample points locating on two neighboring mmode lines on both sides of the generated mmode line which have the same detected depth as the mapping point.

* * * * *